United States Patent [19]

Geen et al.

[11] Patent Number: 5,220,024
[45] Date of Patent: Jun. 15, 1993

[54] PROCESS FOR THE PREPARATION OF PURINE DERIVATIVES AS ANTIVIRAL AGENTS

[75] Inventors: Graham R. Geen, Harlow; Trevor J. Grinter, Betchworth; Stephen Moore, Epsom, all of England

[73] Assignee: Beecham Group p.l.c., Brentford, England

[21] Appl. No.: 588,569

[22] Filed: Sep. 26, 1990

[30] Foreign Application Priority Data

Sep. 28, 1989 [GB] United Kingdom ............... 8922076

[51] Int. Cl.$^5$ ............... C07F 9/6524; C07D 473/18; C07D 473/32
[52] U.S. Cl. ............... 544/244; 544/276; 544/277; 560/219
[58] Field of Search ............... 544/244, 276, 277

[56] References Cited

U.S. PATENT DOCUMENTS

| | | | |
|---|---|---|---|
| 4,798,833 | 1/1989 | Johansson et al. | 544/277 |
| 4,910,307 | 3/1990 | Wyatt | 544/276 |
| 4,942,166 | 7/1990 | Harnden et al. | 544/277 |
| 4,988,703 | 1/1991 | Norbeck et al. | 544/277 |
| 5,017,701 | 5/1991 | Grinter et al. | 544/277 |

FOREIGN PATENT DOCUMENTS

| | | |
|---|---|---|
| 182024 | 5/1986 | European Pat. Off. |
| 0186640 | 7/1986 | European Pat. Off. |

*Primary Examiner*—Mukund Shah
*Assistant Examiner*—E. Bernhardt
*Attorney, Agent, or Firm*—Hopgood, Calimafde, Kalil, Blaustein & Judlowe

[57] ABSTRACT

A process for the preparation of a compound of formula (A):

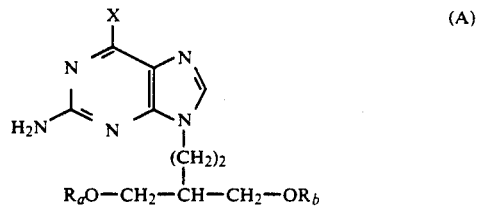

wherein X is hydrogen, hydroxy, chloro, $C_{1-6}$ alkoxy or phenyl $C_{1-6}$ alkoxy and $R_a$ and $R_b$ are hydrogen, including acyl and phosphate derivatives thereof; which process comprises:

i) the preparation of a compound of formula (I):

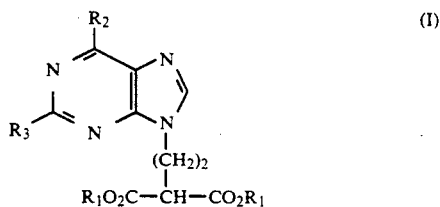

wherein $R_1$ is $C_{1-6}$ alkyl, or phenyl $C_{1-6}$ alkyl in which the phenyl group is optionally substituted; $R_2$ is hydrogen, hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group or a protected amino group, which process comprises the reaction of a compound of formula (II):

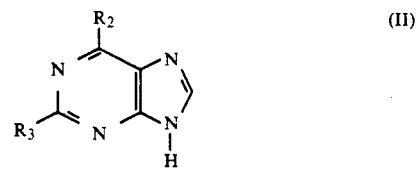

with a compound of formula (VII):

(Abstract continued on next page.)

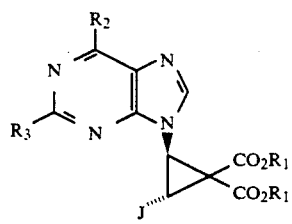

(VIII)

followed by reduction of the compound of formula (VIII) to give a compound of formula (I) as hereinbefore defined; and, as necessary or desired, interconverting variables $R_1$, $R_2$ and $R_3$ to further values of $R_1$, $R_2$ and $R_3$;

(ii) the conversion of the resulting compound of formula (I) to a compound of formula (A) by converting variable $R_3$, when other than amino, to amino, reducing the ester groups $CO_2R_1$ to $CH_2OH$ and optionally forming acyl or phosphate derivatives thereof, and as necessary or desired converting variable $R_2$ in the compound of formula (I) to variable X in the compound of formula (A).

9 Claims, No Drawings

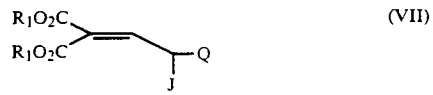

(VII)

wherein Q is a leaving group, J is hydrogen or halo and $R_1$ is as hereinbefore defined; to give a compound of formula (VIII):

PROCESS FOR THE PREPARATION OF PURINE DERIVATIVES AS ANTIVIRAL AGENTS

The present invention relates to a novel chemical process for the preparation of compounds which are useful intermediates in the preparation of pharmaceutically active compounds, and to novel intermediates used in that process.

EP-A-0141927 (equivalent to U.S. Pat. No. 5,075,445, incorporated herein by reference) and EP-A-0182024 (equivalent to U.S. patent application Ser. No. 285,399, filed Dec. 15, 1988, incorporated herein by reference) describe, inter alia, compounds of formula (A):

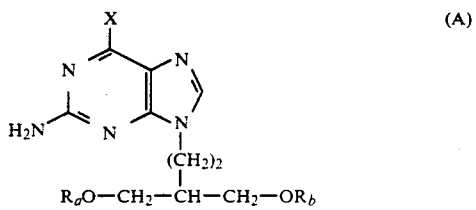

wherein X is hydrogen, hydroxy, chloro, $C_{1-6}$ alkoxy or phenyl $C_{1-6}$ alkoxy and $R_a$ and $R_b$ are hydrogen, including acyl and phosphate derivatives thereof.

The above publications disclose a process for the preparation of compounds of formula (A) which involves the reaction of purine derivatives, including compounds of formula (B):

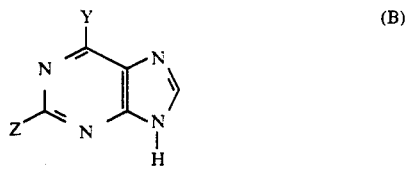

wherein Y is chloro, hydroxy, $C_{1-6}$ alkoxy, phenyl $C_{1-6}$ alkoxy or amino, and Z is chloro, amino or acylamino, with compounds of formula (C):

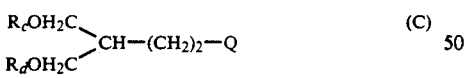

in which $R_c$ and $R_d$ are each independently acyl or together form a cyclic acetal or cyclic carbonate group and Q is a leaving group such as, chlorine, bromine or iodine, preferably iodine.

This process has the disadvantage that compounds of formula (C) are not readily available and must be prepared individually via multi-stage syntheses.

EP-A-302644 (equivalent to U.S. patent application Ser. No. 506,587, filed Apr. 1990, incorporated herein by reference) describes a process for the preparation of compounds or formula (A) which uses a readily available or easily prepared starting material in place of the intermediates of formula (C), which process comprises:

(i) the preparation of a compound of formula (I):

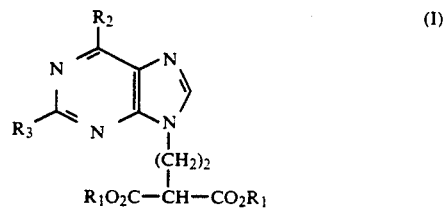

wherein $R_1$ is $C_{1-6}$ alkyl, or phenyl $C_{1-6}$ alkyl in which the phenyl group is optionally substituted; $R_2$ is hydrogen, hydroxy, chlorine, $C_{1-6}$ alkoxy, phenyl $C_{1-6}$ alkoxy or amino; and $R_3$ is halogen, $C_{1-6}$ alkylthio, $C_{1-6}$ alkylsulphonyl, azido, an amino group or a protected amino group, which preparation comprises the reaction of a compound of formula (II):

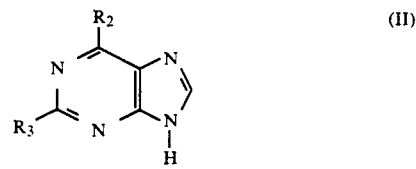

wherein $R_2$ and $R_3$ are as defined for formula (I) with:
(a), a compound of formula (III):

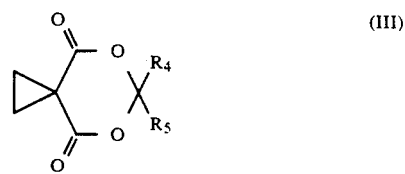

wherein $R_4$ and $R_5$ are independently hydrogen, $C_{1-6}$ alkyl, or phenyl, or $R_4$ and $R_5$ together are $C_{5-7}$ cycloalkyl, to give a compound of formula (IV):

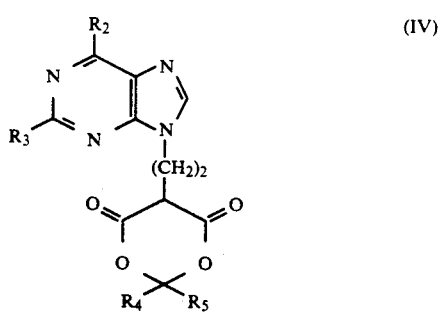

or
(b), a compound of formula (V):

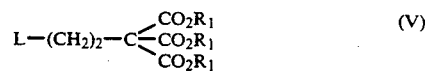

wherein L is a leaving group and $R_1$ is a defined for formula (I), to give a compound of formula (VI):

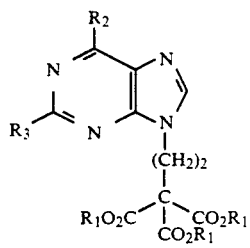

and thereafter converting the intermediate compound of formula (IV) to a compound of formula (I) via transesterification, or the intermediate compound of formula (VI) to a compound of formula (I) via decarboxylation, and, as necessary or desired, interconverting variables $R_1$, $R_2$ and $R_3$ to further values of $R_1$, $R_2$ and $R_3$;

(ii) the conversion of the resulting compound of formula (I) to a compound of formula (A) by converting variable $R_3$, when other than amino, to amino, reducing the ester groups $CO_2R_1$ to $CH_2OH$ and optionally forming acyl or phosphate derivatives thereof, and as necessary or desired converting variable $R_2$ in the compound of formula (I) to variable X in the compound of formula (A).

A novel process for the preparation of a compound of formula (A) has now been discovered, which utilises a readily available intermediate and gives an overall improved yield and/or involves less stages than the process of EP-A-302644.

Accordingly, the present invention provides a process for the preparation of a compound of formula (A) which process comprises:

(i) the preparation of a compound of formula (I) as hereinbefore defined, which preparation comprises the reaction of a compound of formula (II) as hereinbefore defined, with a compound of formula (VII):

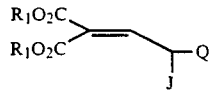

wherein Q is a leaving group, J is hydrogen or halo and $R_1$ is as hereinbefore defined; to give a compound of formula (VIII):

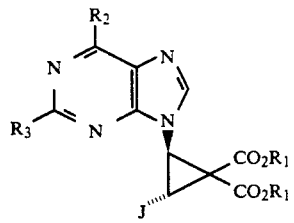

followed by reduction of the compound of formula (VIII) to give a compound of formula (I) as hereinbefore defined; and, as necessary or desired, interconverting variables $R_1$, $R_2$ and $R_3$ to further values of $R_1$, $R_2$ and $R_3$;

(ii) the conversion of the resulting compound of formula (I) to a compound of formula (A) by converting variable $R_3$, when other than amino, to amino, reducing the ester groups $CO_2R_1$ to $CH_2OH$ and optionally forming acyl or phosphate derivatives thereof, and as necessary or desired converting variable $R_2$ in the compound of formula (I) to variable X in the compound of formula (A).

As used herein, the term $C_{1-6}$ alkyl includes groups in which the alkyl moiety is straight or branched, favourably contains 1 to 4 carbon atoms and is preferably methyl. Substituents for phenyl when optionally substituted include one or two of hydroxy, $C_{1-6}$ alkyl, $C_{1-6}$ alkoxy and halogen, such as fluoro, chloro, bromo and iodo.

Values for X in compounds of formula (A) include hydrogen, hydroxy and $C_{1-6}$ alkoxy, for example methoxy. When X is hydroxy it will be appreciated that compounds of formula (A) exist in more than one tautomeric form.

Values for $R_a$ and $R_b$ in compounds of formula (A) include hydrogen and acyl such as $C_{2-5}$ alkanoyl, for example acetyl.

Values for $R_1$ in compounds of formula (I) include $C_{1-4}$ alkyl, for example methyl and ethyl.

Values for $R_2$ in compounds of formula (I) include hydrogen, chlorine, and $C_{1-4}$ alkoxy, for example methoxy.

Suitable values for $R_3$ when a protected amino group include $C_{2-5}$ alkanoylamino such as acetylamino or pivaloylamino, aroyl such as benzoyl, and arylmethyl such as benzyl.

Values for $R_3$ in compounds of formula (I) include amino, halogen for example chlorine, and protected amino such as $C_{2-5}$ alkanoylamino, for example acetylamino.

When $R_2$ in compounds of formula (II) is hydrogen, examples of $R_3$ include halogen for example chlorine, and amino When $R_2$ in compounds of formula (II) is chlorine, examples of $R_3$ include halogen for example chlorine, amino, and acetylamino. Preferably $R_2$ in compounds of formula (II) is chlorine and $R_3$ in compounds of formula (II) is amino.

The leaving group Q in compounds of formula (VII) is usually a halogen atom, preferably bromine or chlorine. J may be hydrogen or a halogen atom, such as bromine. Preferably $R_1$ is an ethyl group.

The reaction of a compound of formula (II) with a compound of formula (VII) may be carried out in an inert solvent for example dimethylformamide, dimethylsulphoxide or acetonitrile, preferably dimethylformamide, in the presence of an inorganic or organic base, over a temperature range from 0° C. to the boiling point of the solvent. Examples of inorganic bases include alkali metal hydrides, alkali metal carbonates such as sodium or potassium carbonate and preferably potassium carbonate. Suitable organic bases are 1,8-diazabicyclo[5.4.0]undec-7-ene and tetramethyl guanidine.

The compound of formula (VIII) is converted to a compound of formula (I) by reduction, preferably by catalytic reduction using a noble metal catalyst, for example palladium on charcoal, in the presence of hydrogen or a hydrogen source such as ammonium formate, in an alcoholic solvent, preferably methanol or ethanol.

Intermediate compounds of formula (VIII) in which $R_2$ is chlorine may be hydrogenolysed directly to give compounds of formula (I) in which $R_2$ is hydrogen. In this case, the reaction preferably takes place in the presence of an organic or inorganic base, such as triethylamine or magnesium oxide.

Variable $R_3$ in compounds of formula (I) may be converted to further values of $R_3$ using conventional procedures. For example, an amine protecting group such as arylmethyl may be removed by hydrogenolysis. Where the intermediate compound of formula (VIII) is subjected to hydrogenolysis reactions as described above, the protecting group will be removed at this intermediary stage. Similarly, variable $R_3$ may be converted from azido to amino by catalytic reduction, and an $R_3$ halogen, alkylthio or alkylsulphonyl group may be converted to an $R_3$ amino group by aminolysis using, for example, ammonia.

Variables $R_1$ and $R_2$ may of course be susceptible to the reaction conditions chosen for interconversion of variable $R_3$. It will be apparent to the skilled chemist that the stage in the reaction sequence at which the transformation of variables, where necessary or desired, is carried out, may be chosen to suit the variables $R_1$, $R_2$ and $R_3$ required in the compound of formula (I).

The compounds of formula (VIII) are novel compounds and form an aspect of the present invention.

Compounds of formula (VIII) may form salts and solvates such as hydrates, and the invention also extends to these forms.

Compounds of formula (VII) are known compounds or are prepared by analogous procedures to those used to prepare known compounds of formula (VII).

Purine derivatives of formula (II) are generally known compounds and processes for their preparation are described in the art relating to purine chemistry. The compound of formula (II) in which $R_2$ is chlorine and $R_3$ is an amino group is 2-amino-6-chloropurine, utilised in the process of the Examples disclosed in EP-A-0141927.

The compounds of formula (I) in which $R_2$ is hydrogen, hydroxy, chloro, $C_{1-6}$ alkoxy or phenyl $C_{1-6}$ alkoxy and $R_3$ is an amino group may be reduced under conventional conditions, for example using sodium borohydride, to the compounds of formula (A) in which X is hydrogen, hydroxy, chloro, $C_{1-6}$ alkoxy or phenyl $C_{1-6}$ alkoxy and $R_a$ and $R_b$ are hydrogen. The compound of formula (A) in which X is hydroxy and $R_a$ and $R_b$ are hydrogen may be obtained under conventional hydrolysis conditions, for example in aqueous sodium hydroxide solution, from compounds of formula (A) in which X is $C_{1-6}$ alkoxy or phenyl $C_{1-6}$ alkoxy and $R_1$ and $R_b$ are hydrogen.

Compounds of formula (A) in which X is hydrogen or hydroxy and $R_a$ and $R_b$ are hydrogen may be converted to further compounds of formula (A) in accordance with the procedures described in EP-A-0182024 and EP-A-0141927.

The following Examples illustrate the invention; the following Description relates to the preparation of an intermediate.

DESCRIPTION

Diethyl-2-chloroethylidene malonate

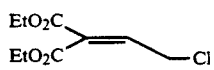

A solution of titanium (IV) chloride (11 ml, 0.1M) in carbon tetrachloride (25 ml) was added dropwise to anhydrous tetrahydrofuran (200 ml) at 0° under nitrogen. On completion of the addition, diethyl malonate (7.6 ml, 50 mM) and anhydrous chloroacetaldehyde (5 g, 63 mM) were added, then a solution of pyridine (16 ml, 0.2M) in anhydrous tetrahydrofuan (35 ml) was added dropwise over 2 hours at 0°. On completion of the addition, the dark mixture was allowed to warm to room temperature, stirred at this temperature for 2 hours, then heated under reflux overnight. The reaction mixture was cooled, water (500 ml) added and the mixture extracted with diethyl ether (2×250 ml). The combined extracts were washed with water (500 ml), saturated sodium bicarbonate solution (500 ml) and brine (500 ml), dried ($MgSO_4$) and evaporated to give a brown oil. Column chromatography of this oil on silica (eluent 1:1 hexane:dichloromethane) afforded the title compound as a pale yellow oil 4.9 g, 44%.

$^1$H N.M.R. ($CDCl_3$): $\delta$1.32(t,3H,$CH_3$), 1.34(t,3H,$CH_3$), 4.30(m,6H,2×$OCH_2$, $CH_2Cl$), 7.01(t,1H,CH).

M.S. (ammonia C.I.). 238(M+$NH_4$)+, 221(M+H)+

Found: C;48.97, H;5.99, Cl;16.30. $C_9H_{13}O_4Cl$. requires: C;48.99, H;5.89, Cl;16.07%.

EXAMPLE 1 a)
2-Amino-6-chloro-9-(2,2-dicarboethoxycyclopropyl)-purine

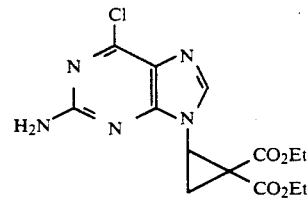

Diethyl-2-bromoethylidene malonate (8.37 g, 32 mM) was added to a stirred mixture of 2-amino-6-chloropurine (5.0 g, 29 mM) and anhydrous potassium carbonate (6.24 g, 45 mM) in N,N-dimethylformamide (140 ml) and the resulting mixture stirred at room temperature overnight. The reaction mixture was then filtered and the filtrate evaporated. H.p.l.c. (C-18 Spherisorb 5μ ODS-2, 15% tetrahydrofuran—85% 0.015M aqueous ammonium acetate) showed two products (Rt 3.8 and 5.6 mins.) corresponding to the N-7 and N-9 alkylated purines in a ratio of 1:8. Column chromatography of the residue on silica (eluent 2.5% methanol-dichloromethane) afforded 8.16 g, 78% of the title compound as a colourless solid. Recrystallisation from butan-1-ol gave fine crystals m.p. 159–160°.

$^1$H N.M.R. ($D^6$-DMSO): $\delta$0.77(t,3H,$CH_3$), 1.23(t,3H,$CH_3$), 2.03(dd,1H,cyclopropyl methylene CH), 2.81(dd,1H, cyclopropyl methylene CH), 3.82(q,2H,$OCH_2$), 4.20(dq,2H,$OCH_2$), 4.37(dd,1H N-CH), 7.02(brs,2H,$NH_2$), 8.17(s,1H,H-8).

M.S. (E.I.). 353m+, 184(m-$C_5H_4N_5Cl$)+.

b)
2-Amino-9-(ethyl-2-carboethoxybutanoate-4-yl)-purine

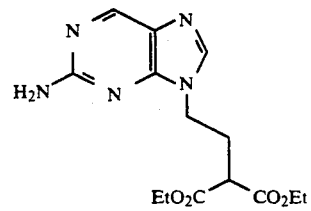

A mixture of 2-amino-6-chloro-9-(2,2-dicarboethoxycyclopropyl)purine (1.19 g, 3.4 mM), 5% palladium on charcoal (0.12 g) and triethylamine (0.37 g, 3.7 mM) was hydrogenated at 50 p.s i.(344.75×10³ Nm⁻²)/80° in ethanol (250 ml) for 18 hrs. H.p.l.c. (C-18 Spherisorb 5µ ODS-2, 30% methanol—70% 0.05M ammonium acetate buffer pH 3.5) indicated the disappearance of starting material Rt 4.2 mins., and a new peak at 5.8 mins. corresponding to the desired product. After cooling, the reaction mixture was filtered and the residue purified by column chromatography on silica (eluent 5% methanol-dichloromethane) to give the title compound (0.41 g, 38%) as an oil which crystallised on standing at ambient temperature.

¹H N.M.R. (D⁶-DMSO) : δ  1.13(t,6H,2xCH₃), 2.33(q,2H,CHCH₂), 3.47(t,1H,CHCH₂), 4.04(dq,4H,2xOCH₂), 4.13(m,2H, N-CH₂), 6.47(brs,2H,NH₂), 8.00(s,1H,H-8), 8.56(s,1H,H-6).

M.S. (C.I.). 322(m+H)+

EXAMPLE 2 a) 2-Amino-9-(2,2-dicarboethoxycyclopropyl)purine

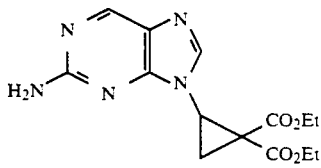

Diethyl-2-bromoethylidene malonate (7.2 g, 27 mM) was added to a stirred mixture of 2-aminopurine (3.67 g, 27 mM) and anhydrous potassium carbonate (5.6 g, 40.5 mM) in N,N-dimethylformamide (50 ml) and the resulting mixture stirred at room temperature overnight. The reaction mixture was then filtered and the filtrate evaporated. Column chromatography of the residue on silica (eluent 5% methanol—chloroform) afforded the title compound as a colourless solid (3.36 g,39%).

¹H N.M.R. (D₆-DMSO): δ 0.72(t,3H,CH₃), 1.24(t,3H,CH₃), 2.03(dd,1H,cyclopropyl methylene CH), 2.83(dd,1H,cyclopropyl methylene CH), 3.78(q,2H,OCH₂), 4.21(dq,2H,OCH₂), 4.38(dd,1H,N-CH), 6.60(brs,2H,NH₂), 8.05(s,1H,H-8), 8.54(s,1H,H-6).

b) 2-Amino-9-(ethyl-2-carboethoxybutanoate-4-yl)-purine

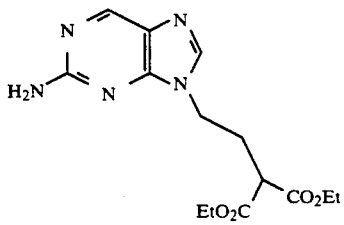

A mixture of 2-amino-9-(2,2-dicarboethoxycyclopropyl)-purine (35.2 g, 0.1M) and 5% palladium on charcoal (10 g) was hydrogenated at 50 p.s.i.(344.75×10³) Nm⁻²/100° in ethanol (250 ml) for 18 hrs. After cooling, the reaction mixture was filtered and the residue purified by column chromatography on silica (eluent 5% methanol—ethyl acetate) to give the title compound (6.5 g, 18%) as an oil which crystallised on standing at ambient temperature.

EXAMPLE 3

2-Amino-6-benzyloxy-9-(2,2-dicarboethoxycyclopropylpurine

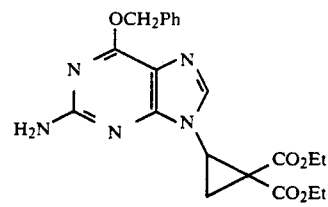

Diethyl-2-bromoethylidene malonate (2.92 g, 11 mM) was added to a stirred mixture of 2-amino-6-benzyloxypurine (2.4 g, 10 mM) and anhydrous potassium carbonate (2.07 g, 15 mM) in N,N-dimethylformamide (40 ml) and the resulting mixture stirred at room temperature for 5 hours. The reaction mixture was then filtered and the filtrate evaporated. Column chromatography of the residual oil on silica (eluent 2.5% methanol—dichloromethane) afforded 2.6 g, 61% of the title compound as a pale yellow oil. Crystallisation from diethyl ether gave off-white crystals m.p. 117–119°.

¹H N.M.R. (D₆-DMSO): δ 0.77(t,3H,CH₃), 1.23(t,2H,CH₃), 1.99(dd,1H,cyclopropyl methylene CH), 2.81(t,1H,cyclopropyl methylene CH), 3.81(q,2H,OCH₂CH₃), 4.20(dq,2H,OCH₂CH3), 4.34(dd,1H,N-CH), 5.49(s,2H,OCH₂Ph), 6.57(brs,2H,NH₂), 7.34–7.51(m,5H,Ph), 7.87(s,1H,H-8).

M.S. (E.I.) 425 m⁺, 241(m-C₉H₁₂O₄)⁺

EXAMPLE 4

2-Amino-6-chloro-9-(2,2-dicarboethoxycyclopropyl)-purine

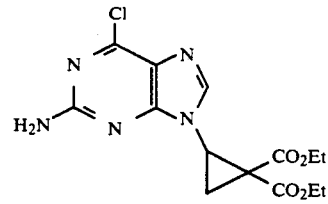

Diethyl-2-chloroethylidene malonate (2.5 g, 11 mM) was added to a stirred mixture of 2-amino-6-chloropurine (1.7 g, 10 mM) and anhydrous potassium carbonate (2.07 g, 15 mM) in N,N-dimethylformamide (40 ml) and the resulting mixture stirred at room temperature for 24 hours. The reaction mixture was then filtered and the filtrate evaporated. H.p.l.c. (C-18 Spherisorb 5µ ODS-2, 15% tetrahydrofuran—85% 0.015M aqueous H ammonium acetate) analysis showed two products (R₁ 3.8 and 5.6 mins.) corresponding to the N-7 and N-9 alkylated purines in a ratio of 1:40. Column chromatography of the residue on silica (eluent 2–4% methanol—dichloromethane) afforded of the title compound as a colourless solid (2.45 g, 69%).

EXAMPLE 5 a) trans-2-Amino-9-(2-bromo-3,3-dicarboethoxycyclopropyl)-6-chloropurine

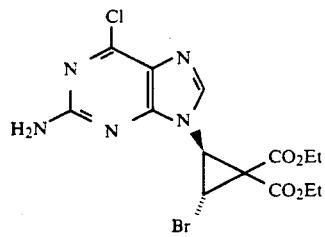

Diethyl-2,2-dibromoethylidene malonate (20.3 g, 59 mM) was added to a stirred mixture of 2-amino-6-chloropurine (10.0 g, 59 mM) and anhydrous potassium carbonate (12.2 g, 88.5 mM) in N,N-dimethylformamide (100 ml) and the resulting mixture stirred at room temperature for 72 hours. The reaction mixture was then filtered and the filtrate evaporated. Column chromatography of the residue on silica (eluent 1% methanol—chloroform) afforded the title compound (8.8 g, 35%) as an off-white solid.

$^1$H N.M.R. (D$_6$-DMSO): δ 0.87(t,3H,CH$_3$), 1.30(t,3H,CH$_3$), 3.92(q,2H,OCH$_2$), 4.33(q,2H,OCH$_2$), 4.75(d,J=5Hz,1H,CH), 5.11(d,J=5Hz,1H,CH), 7.01(brs,2H,NH$_2$), 8.25(s,1H,H-8).

b) 2-Amino-9-(ethyl-2-carboethoxybutanoate-4-yl)-purine

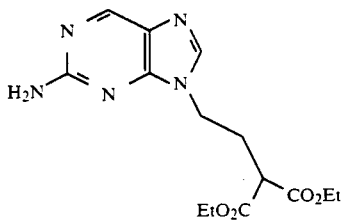

A mixture of trans 2-amino-9-(2-bromo-3,3-dicarboethoxycyclopropyl)-6-chloropurine (8.6 g, 20 mM), 5% palladium on charcoal (2 g) and triethylamine (4.04 g, 40 mM) was hydrogenated at 50 p.s.i. (344.75×10$^3$ Nm$^{-2}$)/100° in ethanol (200 ml) for 18 hours. After cooling, the reaction mixture was filtered and the residue taken up in chloroform (100 ml), washed with water (100 ml), dried (MgSO$_4$) and evaporated to give an oil (5.8 g, 91%) which crystallised on standing.

We claim:

1. A process for the preparation of a compound of formula (A):

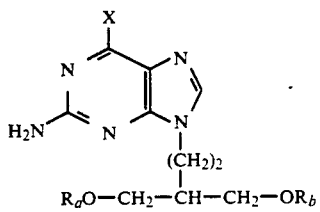

wherein X is hydrogen, hydroxy, chloro, C$_{1-6}$ alkoxy or phenyl C$_{1-6}$ alkoxy and R$_a$ and R$_b$ are hydrogen, and C$_{2-5}$ alkanoyl phosphate derivatives thereof; which process comprises:

i) the preparation of a compound of formula (I):

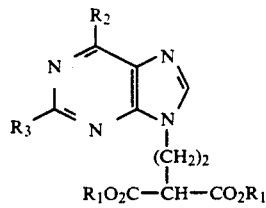

wherein R$_1$ is C$_{1-6}$ alkyl, or phenyl C$_{1-6}$ alkyl in which the phenyl group is optionally substituted by one or two moieties selected from among hydroxy, C$_{1-6}$ alkyl, C$_{1-6}$ alkoxy, and halogen; R$_2$ is hydrogen, hydroxy, chlorine, C$_{1-6}$ alkoxy, phenyl C$_{1-6}$ alkoxy or amino; and R$_3$ is halogen, C$_{1-6}$ alkylthio, C$_{1-6}$ alkylsulphonyl, azido, an amino group or a protected amino group, by a process which comprises the reaction of a compound of formula (II):

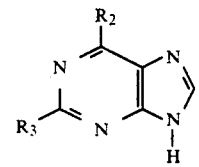

with a compound of formula (VII):

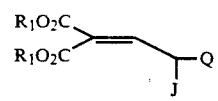

wherein Q is a halo leaving group, J is hydrogen or halo and R$_1$ is as hereinbefore defined; to give a compound of formula (VIII):

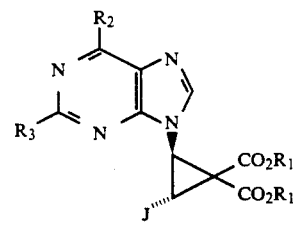

followed by a reduction of the compound of formula (VIII) to give a compound for formula (I) as hereinbefore defined; and optionally interconverting R$_1$, R$_2$ and R$_3$ to other moieties from among those by which R$_1$, R$_2$ and R$_3$ are hereinbefore defined; and ii) the conversion of the resulting compound of formula (I) to a compound of formula (A) by converting variable R$_3$, when other than amino, to amino, reducing the ester groups CO$_2$R$_1$ to CH$_2$OH and optionally forming C$_{2-5}$ alkanoyl or phosphate derivatives thereof, and when necessary converting variable R$_2$ in the compound of formula (I) to variable X in the compound of formula (A).

2. A process according to claim 1 wherein J is hydrogen in the compound of formula (VII).

3. A process according to claim 1 wherein $R_2$ in formula (II) is chlorine.

4. A process according to claim 1 wherein X is hydrogen in the resulting compound of formula (A).

5. A process according to claim 1 wherein $R_a$ and $R_b$ are both acetyl.

6. A process according to claim 1 wherein $R_1$ is ethyl.

7. A process according to claim 1 wherein $R_3$ is amino.

8. An intermediate compound of formula (VIII)

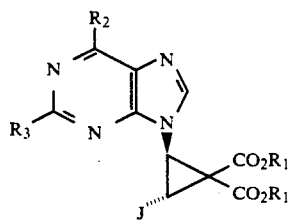

wherein $R_1$ is $C_{1-6}$ alkyl, or phenyl $C_{1-6}$ alkyl in which the phenyl group is optionally substituted by one or two of hydroxy, $C_{1-6}$ alkyl, $C_{1-6}$ alkoxy, or halogen; $R_2$ is hydrogen, hydroxy, chloro, $C_{1-6}$ alkoxy, phenyl $C_{1-6}$ alkoxy or amino; $R_3$ is halogen, $C_{1-6}$ alkylthio, $C_{1-6}$ alkylsulphonyl, azido, an amino group or a protected amino group; and J is hydrogen or halo.

9. A compound selected from the group consisting of:
2-amino-6-chloro-9-(2,2-dicarboethoxycyclopropyl-purine,
2-amino-9-(2,2-dicarboethoxycyclopropyl)purine,
2-amino-6-benzyloxy-9-(2,2-dicarboethoxycyclo-propylpurine,
trans-2-amino-9-(2-bromo-3,3-dicarboethoxycyclo-propyl)-6-chloropurine.

* * * * *